United States Patent [19]

Fries Hastings

[11] Patent Number: 5,242,950

[45] Date of Patent: Sep. 7, 1993

US005242950A

[54] TREATMENT OF MACULAR DEGENERATION

[75] Inventor: Barbara A. Fries Hastings, Tulsa, Okla.

[73] Assignee: Somerset Pharmaceuticals, Inc., Tampa, Fla.

[21] Appl. No.: 872,839

[22] Filed: Apr. 23, 1992

[51] Int. Cl.$^5$ ............................................ A61K 31/135
[52] U.S. Cl. ...................... 514/654; 514/912
[58] Field of Search ................. 514/654, 646, 912

[56] References Cited

U.S. PATENT DOCUMENTS

| | | | |
|---|---|---|---|
| 4,861,800 | 8/1989 | Buyske | 514/646 |
| 4,868,218 | 9/1989 | Buyske | 514/646 |
| 4,925,878 | 5/1990 | Bodo et al. | 514/646 |

OTHER PUBLICATIONS

Age-Related Macular Degeneration, Lawrence A. Yannuzzi et al, pp. 1-64.
New York Academy of Medicine Opthamology Section Meeting, Dec. 7, 1987.
For My Patient-Macular Degeneration, Howard Schatz MD et al, pp. 1-51 The Retina Research Fund 1989.
The Current Status of Monoamine Oxidase and its Inhibitors, Jarrott et al The Medical Journal of Australia vol. 146, pp. 634-638, Jun. 15, 1987.
Etiology of Parkinson's Disease: Current Concepts, Roger C. Duvoisin Clinical Neuropharmacology, vol. 9, Suppl. 1 pp. S3-S21 (1986).
Changes in Local Cerebral Glucose Utilization Associated with Parkinson's Syndrome Induced by 1-Methyl-4-Phenyl-1,2,3,6-Tetrahydropyridine (MPTP) in the Primate, L. J. Porrino et al Life Sciences, vol. 40, pp. 1657-1664 (1987).
Senile Macular Degeneration, Philip L. Penfold et al. Invest. Opthalmology and Visual Science, vol. 27, No. pp. 364-371 (1986).
Studies on the Effect of 1-Methyl-4-Phenyl-1,2,3-,6-Tetrahydropyridine (MPTP) on Central Catecholamine Neurons in C57 BL/6 Mice. Comparison with Three Other Strains of Mice, Sundstrom et al, Brain Research, 405 (1982) pp. 26-38.
Dysfunction and Death of Neurons in Human Degenerative Neurological Diseases and in Animal Models, Donald L. Price et al CIBA Foundation Symposium 126 pp. 30-48 (1987).
Role of B-Type Monoamine Oxidase Inhibition in the Treatment of Parkinson's Disease, Joseph Knoll. Movement Disorders, pp. 53-81 (1986).
Neurology of the Viral System, pp. 75-97 (1967).
Correlative Anatomy of the Nervous System, Elizabeth Crosby et al pp. 434-463 (1962).

*Primary Examiner*—Zohreh A. Fay
*Attorney, Agent, or Firm*—Mathews, Woodbridge & Collins

[57] ABSTRACT

A method of treating macular degeneration is disclosed which comprises administering to a patient suffering from the disease a therapeutically effective amount of L-deprenyl or a pharmaceutically acceptable acid addition salt thereof for a period of time sufficient to ameliorate the disease.

5 Claims, No Drawings

TREATMENT OF MACULAR DEGENERATION

This invention pertains to the treatment of human beings suffering from macular degeneration through administration of L-deprenyl or a pharmaceutically acceptable acid addition salt thereof.

BACKGROUND OF THE INVENTION

According to Penfold et al., Senile Macular Degeneration, *Investigative Ophthalmology and Visual Science*, 1986, 27, pp. 364–371, macular degeneration is one of the leading registered causes of blindness in the United States and in other Western countries.

Loss of central vision in macular degeneration occurs as a result of atrophy of the retinal pigment epithelium. There have been reports of histiocytic and giant cells in the areas of breaks in Bruch's membrane and subretinal neovascular membranes. Light and electron microscope studies of the atrophic cells in senile macular degeneration patients, carried out post mortem, show retinal epithelium cellular elements are destroyed, with the pigment being clumped and adhered to Bruch's membrane. These morphological studies suggest an inflammatory process induced by a degradation product or irritant in the area of the destroyed cells.

Macular degeneration of the retina is a progressive degeneration of the pigmented cells of the retina of unknown cause. The retina has a similar topographical layer arrangement of cytoarchitecture as the brain.

The six layers of the retina carry out the function of transmitting light stimuli into a neuronal excitation. The neuronal stimulus travels from the retinal structures through the optic nerve, then through the brainstem structure of the lateral geniculate, and thereafter through the optic radiations to the occipital final recipient special sensory cortical neurons.

The layers of the retina consist of a neuroectodermal layer of rods and cones, an intermediate layer of bipolar cells, horizontal cells and Muller's cells, and the inner layers containing ganglion cells, glia, nerve fibers, and internal limiting membrane.

The rods and cones are the photoreceptors and consist of outer segments of laminated plates of cells containing photoreceptive pigment and inner segments with dense packing of mitochondria.

The macula in the human retina has special cones and a dense concentration of ganglion cells which permit high resolution of visual acuity.

Pigmented cells occur in the red nucleus, substantia nigra, and locus coeruleus in the brain. The pigmented cells of the retina are hexagonal cells lying just externally to the rods and cones layer of the retina. These cells provide a sheathing or insulation of melanin pigment and also provide the Vitamin A substrate for the photosensitive pigments in the rod and cone cells.

Three forms of macular degeneration have been identified: the "dry" form, the "wet" form, and pigment epithelial detachment (PED). The dry form occurs in approximately 85 to 90% of patients with macular degeneration. The wet form, which can be more severe, occurs in only about 10% of patients. The PED occurs in less than 5% of the patients.

One of the most common forms of treatment for the wet form of macular degeneration is laser surgery. In the wet form of macular degeneration abnormal blood vessels grow under the retina and lift the retina up. These abnormal blood vessels are called subretinal neovascularization or SRNV. These abnormal blood vessels bleed, leak fluid, and lift up the retina. As a result, vision is reduced. A patient with this type of macular degeneration will lose ability to see unless laser treatment is promptly instituted. Abnormal blood vessels also may form in PED and laser surgery again is indicated here.

To date there has been no successful treatment of macular degeneration with pharmaceutical agents. According to a Symposium on Age-Related Macular Degeneration presented at a meeting of the Section on Ophthalmology of the New York Academy of Medicine, Dec. 7, 1987, moderated by Lawrence A. Yannuzzi, pp. 1–61, nutrition therapy has been used in treating macular degeneration. Copper, zinc, and selenium have been employed as have lipotriad and nicotinic acid. None of these agents really has proven to be successful.

Dimethyl sulfoxide also has shown potential in the prophylaxis against the development and progression of age-related macular degeneration. This agent has had clinical application as a scavenger for free radicals in the treatment of bladder cancer but no conclusion has been reached that the compound really is effective in the treatment of macular degeneration.

The compound L-deprenyl, a selective MAO-B inhibitor, has not been used heretofore in the treatment of macular degeneration. The indications of the compound include treatment of depression, Parkinson's Disease, and Alzheimer's Disease. See U.S. Pat. No. 4,861,800.

DETAILED DESCRIPTION

L-deprenyl or a pharmaceutically acceptable acid addition salt thereof, especially the hydrochloride, is administered orally or transdermally to patients suffering from macular degeneration to offset the effects of this disease.

Oral administration of L-deprenyl to a patient suffering from macular degeneration in a daily dose of from about 5 to about 15 mg, preferably 10 mg, has significantly retarded the progress of this disease.

Preferably the drug is administered orally in 5 mg doses b.i.d. For such routes of administration, the compound is combined with one or more pharmaceutically acceptable inert carrier and formulated as a tablet, capsule, caplet or other conventional orally administrable form.

The dose should be titrated to individual patient's response. Since L-deprenyl is a selective inhibitor of MAO-B, the patient's response should be monitored for signs of untoward side effects associated with inhibition of MAO-A, such as hypertension and/or fluctuations in body temperature, which may occur at doses substantially above that at which MAO-B selectivity is observed; e.g. above about 0.1 mg/kg of body weight.

L-deprenyl also can be administered transdermally as an ointment or from a transdermal patch (see e.g. U.S. Pat. No. 4,861,800). When the transdermal route is employed, the daily dosage of L-deprenyl will be between about 5 and about 50 mg.

A typical ointment base can have the following composition in admixture with 3 parts of L-deprenyl:

| | |
|---|---|
| Polyethylene glycol 6000 diastearate | 5 to 15% |
| Polyethylene glycol 1540 | 15 to 25% |
| Butylated hydroxytoluene | 0.1 to 0.5% |

| | |
|---|---|
| -continued | |
| Polyethylene glycol 300 | Balance |

A typical transdermal patch is prepared by dissolving 5 to 50 mg of the L-deprenyl in a mixture of mineral oil and polyisobutylene to provide a liquid reservoir of active drug. The reservoir is enclosed in a sealed, flat, disc-shaped pouch, 1 to 6 cm in diameter. The top of the pouch consists of a thin aluminized polyester film that is impermeable to the pouch contents. The bottom of the pouch (which will be in contact with the skin in use) consists of a thin polypropylene membrane which is slowly porous to L-deprenyl, allowing the drug to continuously come into contact with the skin, so long as the bottom of the pouch is in contact with the skin. The bottom of the pouch also includes a thin coat of a hypoallergenic silicone adhesive operable to hold the patch firmly to the skin without impeding the permeation of the drug through the membrane. A protective strip of siliconized polyester film can cover the polypropylene membrane prior to application. The polyester film is impermeable to the liquid mixture and thus protects the pouch's therapeutic contents during storage but is removed prior to application to the skin.

A Phase I study protocol was presented to the Food and Drug Administration, since the drug L-deprenyl had not as of that time become available for any use in the United States. A protocol for one patient and one age-matched control was approved. After six months, the results were presented to the FDA; and a request for permission to carry out a Phase II study protocol was submitted. A protocol for additional patients and age-matched controls was approved. The latter study will be outlined.

Two patients were studied. Two age-matched controls also were followed and examined at the same intervals.

L. E., a 76 year old woman, had noted poor vision in her right eye of nine years duration and in her left eye of five years duration. There had been progression of central loss of acuity and distortion of images requiring significant magnification to read and, even with magnification, newspaper print, letters, or bank statements were not possible to be seen. General health was excellent, and she was on no medication. Her ophthalmologic exam revealed O.D. 20/400, O.S. 20/200 acuity, normal lens, optics discs, and intra-ocular pressure. The peripheral retina of both eyes revealed moderate reticular pigmentary degeneration. Centrally, the right eye showed marked degenerative changes with pigment epithelial migration, atrophy, diffuse serous fluid, and in the infra temporal area, hemorrhage. The left eye also showed severe degenerative changes but not hemorrhage. Fluorescein angiography revealed disciform degeneration of most of the central areas, worse on the right and measuring three disc diameters vertically and horizontally on the left, including the foveal avascular zone. There being no leakage or neovascular proliferation, laser photocoagulation therapy was not indicated.

Clinically, the patient could read with maximal magnification of low vision aids, but could not manipulate dials on a stove, sew, or thread a needle, nor could she distinguish colors, ("everything was beige or yellow or black"), or perceive variable surfaces in order to walk without assistance.

B. R., a 70 year old man, had a five year history of gradual progressive deterioration of visual acuity in his right more than left eye. He had mild essential hypertension and early Parkinson's Disease and was taking a regimen of Catapres and Sinemet. His ophthalmologic exam revealed finger counting acuity on the right, 20/80 on the left, normal intraocular pressures, nuclear sclerotic changes bilaterally, and central retinal pigmentary epithelium degeneration and serous leaking bilaterally. His fluoroscein angiogram revealed foveal retinal pigment detachment on the right. Laser photocoagulation was carried out. Cataract removal and lens implantation was performed on the right, resulting in improvement of the right visual acuity to 20/400. Clinically, the patient could not use his tools, watch television, read letter, magazine or newspaper print, drive, nor appreciate any color distinctions.

The patients were given L-deprenyl 5 mg b.i.d. (8 a.m. and 12 noon) for two years. They were assessed with a baseline laboratory profile including CBC, SGOT, SGPT, alkaline phosphatase, and electrolytes, which was repeated every six months throughout the two years. Ophthalmologic examination was carried out every six months, and fluoroscein angiogram was carried out at baseline and one year intervals. Visual fields were attempted to be carried out at different intervals but were considered invalid or too difficult by the patient because of distortion of images subjectively. Fransworth hue color testing was attempted on multiple occasions with each patient and abandoned because of variability of responses.

RESULTS

L. E. had distinct improvement in measurable acuity, from O.D. 20/400 to 20/100 and O.S. 20/200 to 20/80 over one year which was improved even further through the second year to 20/60 bilaterally. She was able to thread a needle, sew white thread against white cloth, handle dials on a stove, read the newspaper with magnification, and perceive where she was walking with more certainty and without any assistance at six months. In twelve months, she could watch and follow a television program, read without her magnifying glass, especially book print as in a novel, and also see accounting columns of figures in sequence, which she had not been able to do for five years. Her three-dimensional distortion of images did not improve, but she was able to see the borders of the deficient scotoma more distinctly, and the areas of "good vision" coalesced into larger, brighter, and more clarified areas. Her color distinction did not improve.

B. R. had improvement in daily functional use of his eyes, could use his tools, read newspaper print with glasses, better perceive and judge his terrain on which walked at twelve months, not at six months. He began to do his own bank statement, read his own bills, read his own letters from his grandchildren and, overall, was less dependent on his wife in daily activities of living at 18 months. He commented that he could definitely see better in the areas where it was previously dim, and also he could scan with his eyes and focus quickly on each object as he scanned. He definitely felt that the areas of poor vision before were improved, and he could see "through and around the holes" in his vision much better. All features of improvement were sustained at two years. On examination, his overall acuity remained the same, but his ability to see "through the holes" allowed him to see O.D. 20/80, O.S. 20/50 in the "better vision" areas, The fundus exam of both patients and the fluorescein angiograms did not change appreciably and even worsened from baseline to the one year point or two year point. No abnormalities were noted in any of the semi-annual laboratory tests.

Both of the age-matched control patients continued to have markedly impaired vision in the range of 20/100–20/200 at onset of the study, and two had deterioration to 20/200–20/400 at the second year point.

A third patient, an 80 year old man, died from unrelated causes (congestive heart failure and pneumonia) nine months into the study. No subjective or objective improvement had been detected at the time of his death.

What is claimed is:

1. A method of treating macular degeneration in a human patient, which comprises administering to said patient a therapeutically effective amount of L-deprenyl or a pharmaceutically acceptable acid addition salt thereof.

2. The method according to claim 1 in which L-deprenyl or a salt thereof is administered orally.

3. The method according to claim 2 in which L-deprenyl or a salt thereof is administered at a dosage of from about 5 to about 15 mg per day.

4. The method according to claim 1 in which L-deprenyl or a salt thereof is administered transdermally.

5. The method according to claim 4 in which L-deprenyl or a salt thereof is administered at a dosage of from about 5 to about 50 mg per day.

* * * * *